United States Patent
Sacanna et al.

(10) Patent No.: US 10,870,096 B2
(45) Date of Patent: Dec. 22, 2020

(54) SELF-INFLATING MICROCAPSULES

(71) Applicant: NEW YORK UNIVERSITY, New York, NY (US)

(72) Inventors: Stefano Sacanna, Brooklyn, NY (US); Theodore Hueckel, Staten Island, NY (US)

(73) Assignee: NEW YORK UNIVERSITY, New York, NY (US)

( * ) Notice: Subject to any disclaimer, the term of this patent is extended or adjusted under 35 U.S.C. 154(b) by 136 days.

(21) Appl. No.: 15/877,213

(22) Filed: Jan. 22, 2018

(65) Prior Publication Data
US 2018/0141019 A1    May 24, 2018

Related U.S. Application Data

(63) Continuation-in-part of application No. PCT/US2016/043699, filed on Jul. 22, 2016.
(Continued)

(51) Int. Cl.
*B01J 13/18*    (2006.01)
*A61K 8/11*    (2006.01)
(Continued)

(52) U.S. Cl.
CPC ............. *B01J 13/18* (2013.01); *A61K 8/11* (2013.01); *A61K 8/8152* (2013.01); *A61K 9/5031* (2013.01); *A61Q 19/00* (2013.01); *B01J 13/14* (2013.01); *B01J 13/20* (2013.01); *A61K 9/5089* (2013.01); *A61K 2800/10* (2013.01); *A61K 2800/412* (2013.01); *C09B 67/0097* (2013.01)

(58) Field of Classification Search
None
See application file for complete search history.

(56) References Cited

U.S. PATENT DOCUMENTS

| 4,001,100 | A | 1/1977 | Haydock |
| 4,753,035 | A | 6/1988 | Ryan et al. |

(Continued)

FOREIGN PATENT DOCUMENTS

| WO | WO-2008/076414 | 6/2008 |
| WO | WO-2014/110148 A1 | 7/2014 |

OTHER PUBLICATIONS

International Search Report and Written Opinion of the ISA/US in PCT/US16/43699, dated Oct. 6, 2016, 9 pages.
(Continued)

*Primary Examiner* — Jeffrey D Washville
(74) *Attorney, Agent, or Firm* — Foley & Lardner LLP

(57) ABSTRACT

A method comprises providing an aqueous solution having an alkaline pH and providing an oil including at least one silsesquioxane compound. The oil is added to the aqueous solution. The oil forms a plurality of silsesquioxane oil droplets suspended in the aqueous solution such that an internal osmotic pressure is generated inside the oil droplets via a chemical reaction. The aqueous solution is allowed to osmotically diffuse into the plurality of oil droplets for a predetermined time. The silsesquioxane oil droplets are polymerized by cross-linking the at least one silsesquioxane compound included in the silsesquioxane oil droplets to form a plurality of solidified microcapsules containing the aqueous solution therewithin.

11 Claims, 3 Drawing Sheets

Related U.S. Application Data

(60) Provisional application No. 62/196,218, filed on Jul. 23, 2015.

(51) Int. Cl.
　　*A61Q 19/00* (2006.01)
　　*B01J 13/14* (2006.01)
　　*A61K 8/81* (2006.01)
　　*A61K 9/50* (2006.01)
　　*B01J 13/20* (2006.01)
　　*C09B 67/02* (2006.01)

(56) References Cited

U.S. PATENT DOCUMENTS

| | | |
|---|---|---|
| 5,156,706 A | 10/1992 | Sephton |
| 5,611,971 A | 3/1997 | Maedera et al. |
| 6,337,089 B1 | 1/2002 | Yoshioka et al. |
| 6,507,989 B1 | 1/2003 | Bowden et al. |
| 7,695,814 B2 | 4/2010 | Gartstein et al. |
| 8,071,685 B2 | 12/2011 | Nosker et al. |
| 2002/0082699 A1 | 6/2002 | Ward et al. |
| 2005/0250856 A1 | 11/2005 | Maskaly et al. |
| 2006/0071357 A1 | 4/2006 | Pilon et al. |
| 2006/0159938 A1 | 7/2006 | Lee et al. |
| 2008/0171077 A1 | 7/2008 | Gray |
| 2008/0175918 A1 | 7/2008 | Laulicht |
| 2008/0234394 A1 | 9/2008 | Hong et al. |
| 2009/0324904 A1 | 12/2009 | Mason |
| 2010/0092393 A1 | 4/2010 | Haghgooie et al. |
| 2010/0233436 A1 | 9/2010 | Mason et al. |
| 2010/0252507 A1 | 10/2010 | Lacharme et al. |
| 2011/0200654 A1 | 8/2011 | Habar |
| 2012/0080878 A1 | 4/2012 | Kecht et al. |
| 2013/0064862 A1 | 3/2013 | Weitz et al. |
| 2015/0004095 A1* | 1/2015 | Finnie .............. C09B 67/0013 424/1.29 |
| 2015/0290113 A1* | 10/2015 | Kim .................. C01B 33/18 424/401 |

OTHER PUBLICATIONS

Bishop, K.J.M., et al., "Nanoscale Forces and Their Uses in Self-Assembly", Small, 2009, 5(14):1600-1630.

Hernandez, C.J., et al., "Colloidal Alphabet Soup: Monodisperse Dispersions of Shape-Designed LithoParticles", The Journal of Physical Chemistry C, 2007, 111(12):4477-4480.

Lu, X., et al., "Preparation and characterization of micron-sized hollow polysiloxane spheres", Chemical Engineering Science, 2007, 62(18-20):4880-4884.

Palacci, J., et al., "Living Crystals of Light-Activated Colloidal Surfers", Sciencexpress, Jan. 31, 2013, 339(6122):936-940.

Rossi, L., et al., "Cholesteric colloidal liquid crystals from phytosterol rod-like particles", Soft Matter, 2011, 7(1):64-67.

Sacanna, S., et al., "Lock and key colloids," Nature, Mar. 25, 2010, 464:575-578.

Sacanna, S., et al., "Magnetic Click Colloidal Assembly", Journal of the American Chemical Society, 2012, 134(14):6112-6115.

Yu, S-H., et al., "The Combination of Colloid-Controlled Heterogeneous Nucleation and Polymer-Controlled Crystallization: Facile Synthesis of Separated, Uniform High-Aspect-Ratio Single-Crystalline $BaCrO_4$ Nanofibers", Advanced Materials, Jan. 16, 2003, 15(2):133-136.

Zoldesi, C.I., et al., "Deformable Hollow Hybrid Silica/Siloxane Colloids by Emulsion Templating", Langmuir, 2006, 22(9):4343-4352.

International Search Report & Written Opinion for PCT/US2011/022990, dated Oct. 19, 2011, 10 pages.

International Search Report & Written Opinion for PCT/US2014/010703, dated Apr. 29, 2014, 6 pages.

* cited by examiner

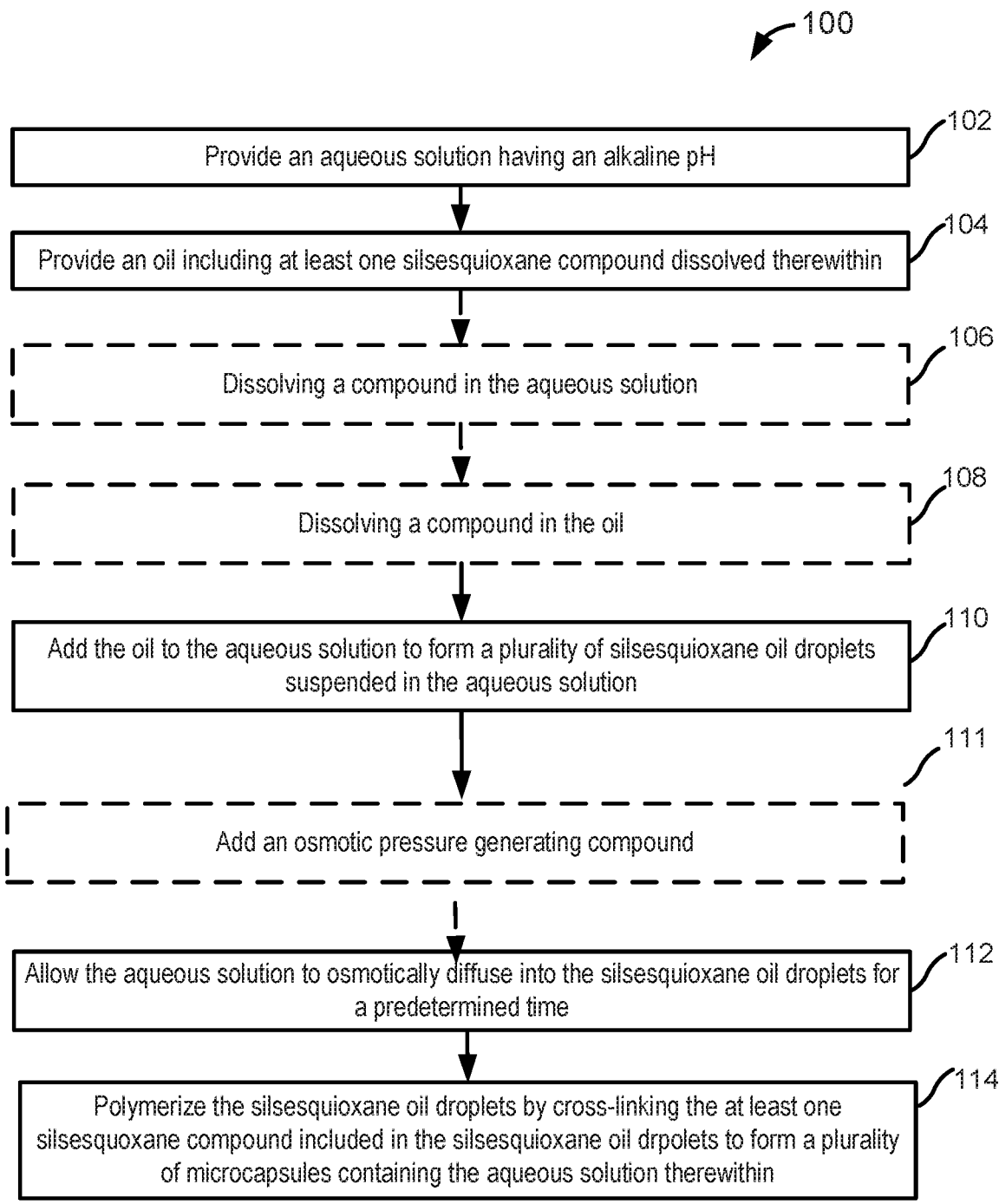

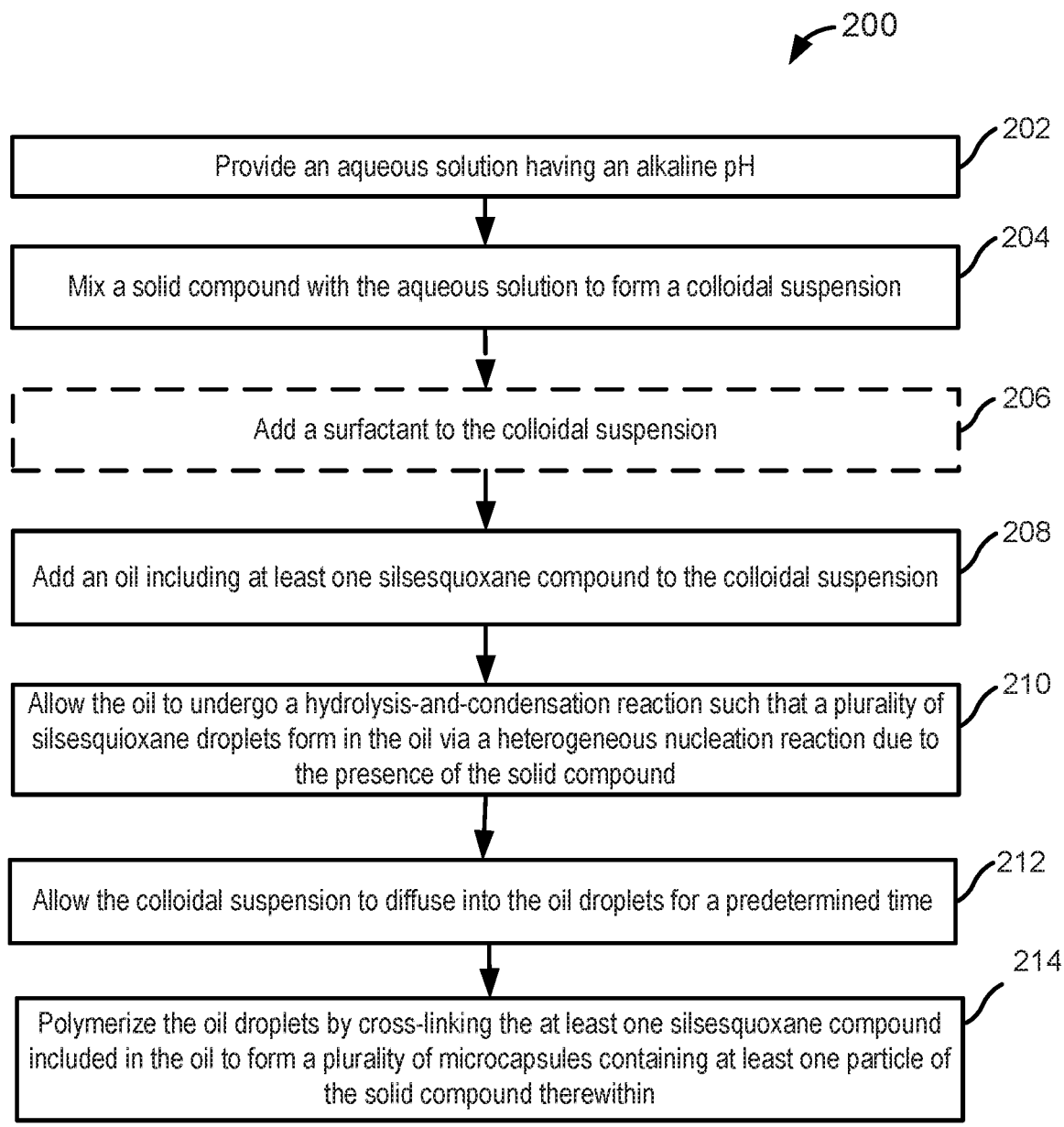

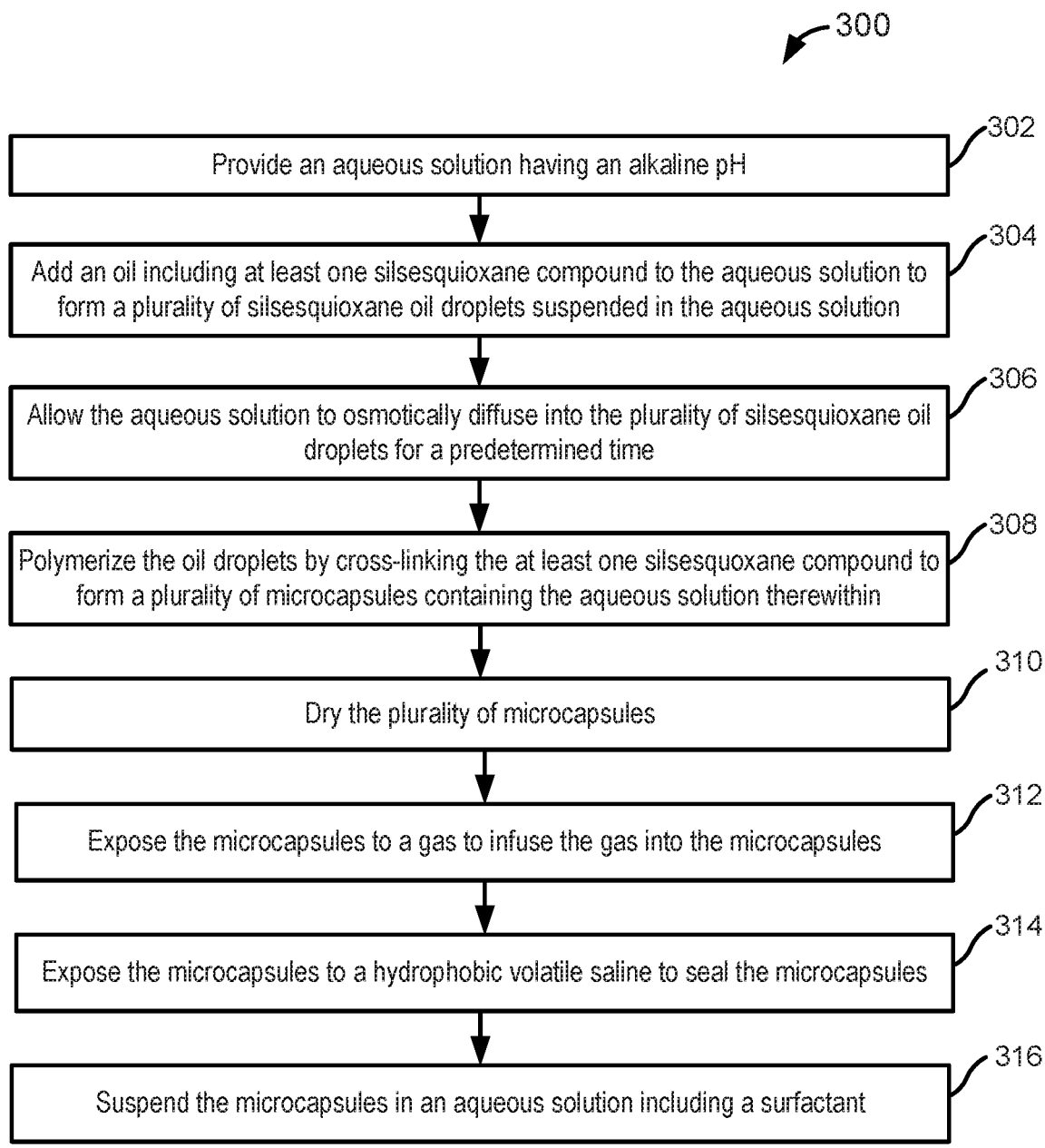

SELF-INFLATING MICROCAPSULES

CROSS-REFERENCE TO RELATED PATENT APPLICATIONS

This application is a continuation-in-part of PCT/US2016/043699 filed Jul. 22, 2016, which claims priority benefit of U.S. Provisional Application No. 62/196,218 filed Jul. 23, 2015, both of which are incorporated herein by reference in their entirety.

TECHNICAL FIELD

The present disclosure relates generally to methods of preparing polymerized oil microcapsules.

BACKGROUND

Microcapsules are colloidal containers that can house or contain drugs, enzymes, food ingredients or other materials on a micrometer scale or nanometer scale. Of particular relevance are microcapsule type micro and nanoparticles capable of encapsulating a payload and releasing the payload on demand. Such microcapsules find uses in various fields including targeted drug delivery, food science, cosmetics, biotechnology, paint industry, agriculture, environmental engineering, etc. Conventional manufacturing processes used to prepare microcapsules, microparticles or nanoparticles, are slow and cumbersome. For example, templating is often used for manufacturing such load carrying microcapsules or particles and consists of depositing material onto a sacrificial template via methods such as interfacial polymerization and layer by layer self-assembly. However, need of a template adds complexity to the synthetic process.

SUMMARY

Embodiments described herein relate generally to methods of preparing microcapsules and in particular, to methods of preparing oil based microcapsules that can contain a solid, liquid or gas therewithin.

In some embodiments, a method comprises providing an aqueous solution having an alkaline pH and providing an oil including at least one silsesquioxane compound. The oil is then added to the aqueous solution such that the oil forms a plurality of silsesquioxane oil droplets suspended in the aqueous solution. Adding the oil to the aqueous solution generates an internal osmotic pressure inside the oil droplets by means of a chemical reaction. The aqueous solution is allowed to osmotically diffuse into the plurality of oil droplets for a predetermined time. The oil droplets are polymerized by cross-linking at least one silsesquioxane oligomer included in the oil to form a plurality of solidified microcapsules containing the aqueous solution therewithin.

In some embodiments, a method comprises providing an aqueous solution having an alkaline pH. A solid compound is mixed with the aqueous solution to form a colloidal suspension. An oil is added to the colloidal suspension. The oil includes at least one silsesquioxane compound. The oil is allowed to undergo a hydrolysis-and-condensation reaction such that a plurality of silsesquioxane oil droplets form via a heterogeneous nucleation due to the presence of the solid compound. The colloidal suspension is allowed to diffuse into the plurality of oil droplets for a predetermined time. The oil droplets are polymerized by cross-linking the at least one silsesquioxane oligomer included in the silsesquioxane oil droplets to form a plurality of solidified microcapsules such that each of the plurality of solidified microcapsules contain at least one particle of the solid compound embedded therewithin.

In some embodiments, a method comprises providing an aqueous solution having an alkaline pH. An oil is added to the aqueous solution. The oil includes at least one silsesquioxane compound. The oil forms a plurality of silsesquioxane oil droplets suspended in the aqueous solution. Furthermore, an internal osmotic pressure is generated inside the oil droplets by means of a chemical reaction. The aqueous solution is allowed to osmotically diffuse into the plurality of silsesquioxane oil droplets for a predetermined time. The silsesquioxane oil droplets are polymerized by cross-linking the at least one silsesquioxane compound included in the silsesquioxane oil droplets to form a plurality of solidified microcapsules containing the aqueous solution therewithin. The plurality of solidified microcapsules are dried. The plurality of solidified microcapsules are exposed to a gas to infuse the gas into the plurality of solidified microcapsules. The plurality of solidified microcapsules are exposed to a hydrophobic volatile silane which seals the plurality of solidified microcapsules to trap the gas therewithin.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 1 is a schematic flow diagram of a method of preparing oil based microcapsules containing an aqueous solution therewithin, according to an embodiment with homogeneous nucleation.

FIG. 2 is a schematic flow diagram of another embodiment of a method of forming oil based microcapsules containing solid particles (seeds) therewithin and utilizing heterogeneous nucleation.

FIG. 3 is a schematic flow diagram of yet another embodiment of a method of forming oil based microcapsules containing a gas therewithin, the illustrated method may follow, for example, step 114 of FIG. 1 or step 214 of FIG. 2.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to methods of preparing microcapsules and in particular, to methods of preparing oil based microcapsules that can contain a solid, liquid, or gas therewithin.

Embodiments of the self-inflating microcapsules described herein may provide numerous benefits including, for example: (1) providing oil based droplets that can self-inflate due to osmotic diffusion by an aqueous solution into the oil to form microcapsules thus allowing rapid loading and fabrication of microcapsules; (2) allowing loading of the microcapsules with an aqueous solution which can contain dissolved compounds, solid particles or a gas; (3) protecting the load contained within the microcapsules; (4) allowing targeted release of the load contained within the microcapsules at specific pH conditions, temperature, or ionic strength; and (5) providing utility in numerous fields including targeted drug delivery, ultrasound imaging, self-healing materials, fragrance release, nutrient preservation, herbicides, insecticides, fungicides, in paints and coatings (e.g., controlled release of biocides), adhesives and sealants (e.g., encapsulation of catalysts, initiators and monomers), personal and household care products (e.g., fragrance delivery), food, nutraceuticals and pharmaceuticals (e.g., taste modifiers, nutrients, additives), etc.

FIG. 1 is a schematic flow diagram of a method 100 for preparing oil microcapsules containing or filled with an aqueous solution according to an embodiment. The method 100 includes providing an aqueous solution having an alkaline pH at 102. The aqueous solution can include, for example water (e.g., deionized water, distilled water or tap water) or a buffer solution, for example, ammonia, HEPES-buffered saline, tris-buffered saline, phosphate buffered saline (PBS), MES, PIPES, Lactated Ringer's solution, Dulbecco's minimum essential media (DMEM), Ham's F-10 media, Ham's F-12 media, minimum essential media (MEM), a cell culture medium, or any other aqueous solution. The pH of the aqueous solution is greater than the neutral pH of 7 (e.g., 8, 9, 10, 11, 12, 13 or 14).

An oil including at least one silsesquioxane compound is provided at 104. The silsesquioxane compound can include a hydrolysable silane monomer and/or a low molecular weight silsesquioxane oligomer. In various embodiments, the oil includes a material that allows for the condensation and hydrolysis of a alkoxy bond, for example alkoxysilane. Specific embodiments include, but are not limited to: organofunctional alkoxysilane molecules including, but not limited to 3-(Trimethoxysilyl)propyl methacrylate, mercaptopropyl trimethoxysilane aminopropyltrimethoxysilane, 3-Chloropropyl)trimethoxysilane. and N-[3-(Trimethoxysilyl)propyl]-N,N,N-trimethylammonium chloride.

Furthermore, at least one silsesquioxane compound can include a compound of formula I:

$$RSiO_{3/2} \quad\quad\quad (I)$$

where:
Si is silicon;
O is oxygen; and
R is hydrogen, alkyl, alkene, aryl or arylene.

Examples of silsesquioxanes include but are not limited to polyhedral oligomeric silsesquioxane (POSS) reagents such as POSS-methacrylates, POSS-Epoxies, POSS-isocyanates, and POSS-Amines. The silsesquioxane oligomers can be synthesized using a hydrolysis and condensation reaction. The silsesquioxane oligomer can be formulated to polymerize under suitable conditions. For example, the silsesquioxane polymer can be formulated to self-polymerize, polymerize when exposed to ultraviolet (UV) light, thermoset (i.e., polymerize at increased temperature), polymerize by a condensation and/or hydrolysis reaction, or polymerize due to changes in pH.

In some embodiments, a compound can also be dissolved in the aqueous solution at 106. In various embodiments, the compound can include a fluorescent dye such as, for example ALEXAFLUOR®, 7-aminoactinomycin D, 8-anilinonaphthalene-1-sulfonic acid, ATTO dyes, auramine-rhodamine stain, benzanthrone, bimane, 9,10-bis(phenylethynyl)anthracene, 5,12-bis(phenylethynyl)naphthacene, bisbenzimide, blacklight paint, brainbow, calcein, carboxyfluorescein, carboxyfluorescein diacetate succinimidyl ester, carboxyfluorescein succinimidyl ester, 1-chloro-9,10-bis(phenylethynyl)anthracene, 2-chloro-9,10-bis(phenylethynyl)anthracene, 2-chloro-9,10-diphenylanthracene, coumarin, DAPI, cark quencher, $DiOC_6$, dylight fluor, epicocconone, flash-EDT2, fluo-3, fluo-4, fluoProbes, fluoro-jade stain, FMN-binding fluorescent proteins, fura-2, fura-2-acetoxymethyl ester, green fluorescent protein, heptamethine dyes, hoechst stain, iminocoumarin indian yellow, indo-1, laurdan, lucifer yellow, luciferin, MCherry, merocyanine, nile red, optical brightener, perylene, phloxine, phycobilin, phycoerythrin, phycoerythrobilin, pyranine, rhodamine, rhodamine 123, rhodamine 6G, ribogreen, RoGFP, rubrene, (E)-stilbene, (Z)-stilbene, sulforhodamine 101, sulforhodamine B, SYBR green I, SYBR safe, synaptopHluorin, tetraphenyl butadiene, tetrasodium tris(bathophenanthroline disulfonate) ruthenium (II), texas red, titan yellow, TSQ, umbelliferone, violanthrone, yellow fluorescent protein, YOYO-1 or any other suitable fluorescent dye.

In other embodiments, the compound can include a pharmaceutical or a nutraceutical. In various embodiment, the compound can include any representative classes of antibiotics, e.g., 1) aminoglycosides, such as gentamycin, kanamycin, neomycin, streptomycin or tobramycin; 2) cephalosporins, such as cefaclor, cefadroxil or cefotaxime; 3) macrolides, such as azithromycin, clarithromycin, or erythromycin; 4) penicillins, such as amoxicillin, carbenicillin or penicillin; 5) peptides, such as bacitracin, polymixin B or vancomycin; 6) quinolones, such as ciprofloxacin, levofloxacin, or enoxacin; 7) sulfonamides, such as sulfamethizole, sulfacetimide; or sulfamethoxazole; 8) tetracyclines, such as doxycycline, minocycline or tetracycline; 8) other antibiotics with diverse mechanisms of action such as rifampin, chloramphenicol, or nitrofurantoin. Other antimicrobial agents, e.g., antifungal agents and antiviral agents can also be used.

In some embodiments, the pharmaceutical or nutraceutical can include a growth factor such as, for example, vascular endothelial cell growth factors (VEGF) (e.g., VEGF A, B, C, D, and E), platelet-derived growth factor (PDGF), insulin-like growth factor (IGF) I and IGF-II, interferons (IFN) (e.g., IFN-α, β or γ), fibroblast growth factors (FGF) (e.g., FGF 1, FGF-2, FGF-3, FGF-4-FGF-10), epidermal growth factor, keratinocyte growth factor, transforming growth factors (TGF) (e.g., TGFα or β), tumor necrosis factor-a, an interleukin (IL) (e.g., IL-1, IL-2, Il-17-IL-18), Osterix, Hedgehogs (e.g., sonic or desert), SOX9, bone morphogenetic proteins (BMP's), in particular, BMP 2, 4, 6, and (BMP-7 is also called OP-1), parathyroid hormone, calcitonin prostaglandins, or ascorbic acid.

In other embodiments, the compound can include anti-inflammatory agents. The anti-inflammatory agents can include, for example non-steroidal anti-inflammatory drugs (NSAIDs) such as, for example, aspirin, choline and magnesium salicylates, celecoxib, diclofenac potassium, diclofenac sodium, diclofenac sodium with misoprostol, diflunisal, etodolac, fenoprofen, flurbiprofen, ibuprofen, indomethacin, ketoprofen, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, any other suitable NSAID or a combination thereof. In some embodiments, the anti-inflammatory agents can include corticosteroids such as, for example, hydrocortisone, hydrocortisone acetate, cortisone acetate, tixocortol pivalate, prednisolone, methylprednisolone, methylprednisolone aceponate, prednisone, triamcinolone acetonide, triamcinolone alcohol, mometasone, mometasone furoate, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, hydrocortisone valerate, flurandrenolide, triamcinolone acetonide, ciclesonide, halobetasol, diflorasone diacetate, fluocinonide, halicinonide, amcinonide, desoximetasone, fluticasone propionate, betamethasone dipropionate, desonide, alclometasone dipropionate, clobetasol propionate, prednicarbate, any other suitable corticosteroid or a combination thereof.

In various embodiments, the compound can also include a polymerizable entity such as acrylic monomers, alkene monomers, vinyl chloride, urethane, or any other polymerizable entity. Any of the compounds can diffuse into oil microcapsules such that the oil microcapsules include the aqueous solution with the compound contained therewithin.

In some embodiments, the method includes dissolving the compound in the oil at 108. In still other embodiments, a plurality of nanoparticles can be suspended in the oil. Such nanoparticles can include magnetic nanoparticles (e.g., magnetite nanoparticles, iron oxide nanoparticles), photocatalytic nanoparticles (e.g., titanium oxide nanoparticles), quantum dots, gold nanoparticles, silver nanoparticles, porous silica nanoparticles, poly(n-isopropylacrylamide) nanoparticles (pNIPAM) nanoparticles, etc. The nanoparticles can get incorporated in the walls of the microcapsules, as described herein. For example, the nanoparticles can include magnetic nanoparticles which are incorporated in the walls of the microcapsules allowing magnetic manipulation of the microcapsules.

The oil is added to the aqueous solution to form a plurality of silsesquioxane oil droplets suspended in the aqueous solution at 110. The hydrophobicity of the oil can urge the oil to form droplets suspended in the aqueous solution. In other words, an oil-aqueous solution microemulsion is formed. In various embodiments, the oil-aqueous solution mixture can be subjected to shaking, vibration, stirring or sonication (e.g., ultrasonication) to form the oil droplets suspended in the aqueous solution.

Adding the oil to the aqueous solution generates an internal osmotic pressure inside the oil droplets by means of a chemical reaction, for example a base catalyzed hydrolysis reaction. Thus, in one embodiment, the silane compound itself provides osmotic pressure. For example, N-[3-(Trimethoxysilyl)propyl]-N,N,N-trimethylammonium chloride, once crosslinked into the oil droplet provides a chloride ion which is essentially pinned inside of the oil droplet to facilitate osmotic flow into the droplet. The important aspect is that something from the oil dissociates into a water-soluble form, which can either be triggered by an external control, e.g. base catalyzed, or happen naturally, e.g. ionization. Other triggers are possible, for instance heating a silane with a metastable moiety that creates an internal osmotic pressure. In one embodiment, an osmotic pressure is generated by add an osmotic pressure generating compound such as a base. FIG. 1 illustrates this as optional step 111. Suitable bases can include sodium hydroxide (NaOH), potassium hydroxide (KOH), tetramethylammonium hydroxide (TMAH) or any other suitable base. In one embodiment, the base is already present in the aqueous solution, for example is used to adjust the pH of the aqueous solution to the alkaline pH. In other embodiments, the base can be separately added to the oil aqueous solution once the oil has been added to the aqueous solution. In one embodiment, the base also includes Azobisisobutyronitrile (AIBN). AIBN can be added to base in any suitable ratio, for example base: AIBN by volume of 1:1, 1:2, 1:3, 1:4, 1:5 or 1:6.

The aqueous solution is allowed to osmotically diffuse into the plurality of silsesquioxane oil droplets for a predetermined time at 112. The inflation happens instantaneously, but can remain inflated and can grow or shrink over that time depending on conditions. For example, in one embodiment, 1-30 min after inflation is the time frame to initialize polymerization. The osmotic pressure difference between the oil droplets and surrounding aqueous solution allows the aqueous solution to diffuse into the silsesquioxane oil droplets. In one embodiment, the osmotic molarity is from 500-2000 mM. This inflates the silsesquioxane oil droplets such that the silsesquioxane oil droplets are filled with a certain amount of the aqueous solution. In this manner, a solution-oil-solution (e.g., water-oil-water) double emulsion is formed.

In various implementations, the predetermined time is sufficient to allow the aqueous solution to diffuse into the silsesquioxane oil droplets until the osmotic pressure inside the silsesquioxane oil droplets is substantially equal to the osmotic pressure of the aqueous solution on the exterior of the oil droplets. In other implementations, the predetermined time to fill the silsesquioxane oil droplets can depend upon the porosity of the oil droplets. Thus, the predetermined time or filling time can be varied to control the amount of aqueous solution that diffuses into the plurality of silsesquioxane oil droplets. The time needed to inflate the droplets (loading time) and the final size of the silsesquioxane oil droplets (or the microcapsules) are controlled by changing temperature and/or the concentration of the catalyst that generates the internal osmotic pressure (for example, the base such as NaOH).

The silsesquioxane oil droplets are polymerized by cross-linking at least one silsesquioxane compound included in the silsesquioxane oil droplets to form a plurality of solidified microcapsules containing the aqueous solution therewithin at 114. The silsesquioxane polymers can be polymerized, for example by a radical polymerization, a condensation and polymerization reaction, exposure to UV light, increasing a temperature of the aqueous solution in which the silsesquioxane oil droplets are suspended, or adjusting a pH of the aqueous solution. In various embodiments, the solidified microcapsules have a diameter in the range of 100 nm to 10 microns. The polymerization cross-links and hardens the silsesquioxane compound included in the oil vesicles yielding the solidified microcapsules which have a solid shell.

In various embodiments, the concentration and/or type of the silsesquioxane compounds (e.g., the silsesquioxane oligomers) can be chosen to provide different physical properties to the shell of the microcapsules. For example, the shell of the microcapsules can be formulated to be soft and deformable, or rigid and brittle. Furthermore, size, polydispersity, wall thickness, surface charge and/or mechanical strength of the microcapsules can be controlled by varying one or more of the polymerization rate, silsesquioxane oligomer concentration, type of silsesquioxane oligomer used, type of oil used and/or type of compound dissolved in the aqueous solution.

In some embodiments in which the aqueous solution includes the compound dissolved therein, the osmotic diffusion also allows the compound to diffuse into the oil droplets so that the silsesquioxane oil droplets contain the aqueous solution with the compound dissolved therein. In particular embodiments, the compound can also bind with the silsesquioxane compound (e.g., a silsesquioxane oligomer) included in the oil, or bind with the oil such that the compound is drawn into the oil droplets. The concentration or amount of the water or aqueous solution soluble compound builds up inside the droplets due to the lower diffusivity of the compound in the oil, thus also driving the aqueous solution (e.g., water) into the oil droplets. This can cause phase separation yielding the solution-oil-solution double emulsion microcapsules.

In some embodiments, in which the compound is included in the oil droplets, a combination of the diffusing and polymerization separates the compound from the oil such that the microcapsules contain the compound with the aqueous solution therewithin. For example, the self-inflation of the oil droplets and subsequent polymerization urges the compound to phase separate from polymerizing oil droplets and be trapped into the microcapsules. In still other embodiments in which nanoparticles are included in the oil, the polymerization traps the nanoparticles into the shell of the microcapsules.

In particular embodiments, the microcapsules can be configured to experience a change in diameters and/or porosity when exposed to a variation in pH or temperature. For example, a change in pH of a solution in which the microcapsules are suspended, from acidic to basic can urge the microcapsules to expand thereby causing an increase in the diameter of the microcapsules. The increase in diameter can increase the porosity of the shell of the microcapsules allowing the aqueous solution and, thereby the compound contained therewithin to leach out of the microcapsules. This can be used to deliver the compound to targeted location. For example, the microcapsule can be used for targeted drug delivery in cells. The microcapsules can have a first diameter within a blood stream of a patient. Once the microcapsules are phagocytized into cells, the higher pH of the cell cytoplasm can cause an increase in the diameter and porosity of the microcapsules thereby allowing the compound contained therewithin to diffuse into the cytoplasm. In other embodiments the microcapsules can also be used as contrast agent in ultrasound imaging. In one embodiment, the silanols can be deprotonated to charge the capsule, resulting in osmotic pressure and expansion of the capsule.

In particular embodiments, the microcapsules can be removed from the aqueous solutions and heated, to promote cross-linking of the silsesquioxane compound. This can dry the microcapsules by evaporating the aqueous solution therewithin. In such embodiments, the microcapsule can be refilled with the aqueous solution by reimmersing the microcapsules in the aqueous solution for a second predetermined time to at least partially fill the microcapsules with the aqueous solution. For example, in one embodiment in a first step is radical polymerization. For radical polymerization, the suspension is heated up to a maximum of 100 to promote polymerization when a radical initiator is present (lower limit 50 Celsius). Radical polymerization may be used alone or in combination with the below. Standing on its own, such provides for increased crosslinking. In a second step calcination may be performed. In calcination, the capsules are died out and then calcinated at higher temperatures, 200 Celsius minimum, max is melting temperature of silica, but preferably about 700 C to promote full calcination in 1-2 hours. The calcination may be used alone or in combination with the other steps. Standing on its own, calcination dries out the capsules forming a dry empty material. In a third step, the capsules may be refilled and/or resuspended. In the refilling and resuspension, dried capsules are interacted with solvent to refill the capsule (due to osmotic pressure) and resuspended the capsules in the solvent. Radical polymerization may precede the drying, but is not required.

In one embodiment, the microcapsules can be "frozen" before inflation, i.e. stabilized in an uninflated form for later use. Freezing of the emulsion includes adding a surfactant, such as F108 surfactant to a final concentration of 0.01%, and then adding hydrochloric acid to a pH of 5. Those particles can be inflated up to a week later by directly adding base to de-acidify the solution.

In some embodiments, rather than inflated hollow microcapsules, solid particles can also be included into the microcapsules. For example, FIG. 2 is a schematic flow diagram of an exemplary method 200 of preparing microcapsules containing solid particles therewithin. The method includes providing an aqueous solution having an alkaline pH at 202. The aqueous solution can include any of the aqueous solutions described before herein.

A solid compound is mixed with the aqueous solution to form a colloidal suspension at 204. For example, the solid can be crushed into a powder and mixed, stirred, shaken or subjected to vibration or ultrasonication to form a colloidal suspension of the solid particles suspended in the aqueous solution. The solid compound can include any compound which is insoluble in the aqueous solution. Such solid compounds can include, for example a pharmaceutical, a nutraceutical, a pigment, a dye, a pesticide, a catalyst or any other suitable solid compound.

In various embodiments, a surfactant is added to the colloidal suspension at 206. Surfactants can be added to affect the stability, charge, and roughness, of the capsules. Furthermore, surfactants can affect nucleation and growth, influencing the capsules dispersity, size, and wall thickness, ultimately affecting properties such as capsule diffusivity and strength. The surfactant can include, for example sodium dodecyl sulfate (SDS), cetrimonium bromide (CTAB), TWEEN® surfactants or any other surfactant. The presence of the surfactant can urge the solid compound to dewet the oil during the microcapsule formation, as described herein. The dewetting can be used to either trap particles of the solid compound within the microcapsules or expel the solid particles from the microcapsules.

An oil including at least one silsesquioxane compound is added to the colloidal suspension at 208. Any suitable silsesquioxane compound (e.g., a hydrolysable silane monomer or a low molecular weight silsesquioxane oligomer) can be used as described before herein, and mixed with any oil as described before herein. The oil is allowed to undergo a hydrolysis-and-condensation reaction so that a plurality of silsesquioxane oil droplets form in the oil via a heterogeneous nucleation reaction due to the presence of the solid compound at 210.

The colloidal suspension is allowed to diffuse into the oil for a predetermined time at 212. Diffusion of the colloidal suspension into the oil droplets also delivers particles of the solid compounds into the oil droplets. The oil droplets therefore self-inflate and are filled with particles of the colloidal suspension.

The oil droplets are polymerized by cross-linking at least one silsesquioxane oligomer included in the oil to form a plurality of solidified microcapsules containing at least one particle of the solid compound therewithin at 214. Any suitable polymerization mechanism can be used. For example, the silsesquioxane oil added to colloidal suspension forms a silsesquioxane oil emulsion which is polymerized, cross-linked or nucleated via a two-step hydrolysis and condensation reaction to form the microcapsule. Each of the plurality of microcapsules can have one or more particles of the solid compound contained therewithin in contrast to the embodiment of FIG. 1 wherein the microcapsule includes no solid material but is hollow. The hydrolysis of the alkoxysilane provides silanols to crosslink, i.e. for formation of the colloidal droplet. This contrasts with the hydrogenation described above for providing osmotic pressure, which occurs within the droplets.

In some embodiments, the microcapsules are prepared to contain a gas therewithin. For example, FIG. 3 is a schematic flow diagram of an exemplary method 300 for preparing microcapsules containing a gas or infused with a gas. The method includes providing an aqueous solution having an alkaline pH at 302. The aqueous solution can include any aqueous solution described before herein.

An oil including at least one silsesquioxane compound is added to the aqueous solution to form a plurality of silsesquioxane oil droplets suspended in the aqueous solution at 304. The oil and the at least one silsesquioxane compound can include any of the silsesquioxane compound and oils described before herein. The aqueous solution is allowed to osmotically diffuse into the plurality of silsesquioxane oil droplets for a predetermined time at 306. As described before herein, this urges the oil droplets to self-inflate and produce oil droplets containing the aqueous solution therewithin.

The silsesquioxane oil droplets are polymerized by cross-linking the at least one silsesquioxane compound included in the silsesquioxane oil droplets to form a plurality of solidified microcapsules containing the aqueous solution therewithin at 308. The oil droplets can be polymerized using any suitable polymerization mechanisms, for example exposure to UV light, self-polymerize, variations in temperature or a hydrolysis and condensation reaction.

The plurality of solidified microcapsules are dried at 310. For example, the plurality of solidified microcapsules can be removed from the aqueous solution using centrifugation, filtering, or any other suitable technique. The plurality of solidified microcapsules can then be dried by heating the plurality of solidified microcapsules or by vacuum drying the plurality of solidified microcapsules. The dried solidified microcapsules are exposed to a gas to infuse the gas into the microcapsules at 312. For example, the microcapsules can be infused with air, oxygen, nitrogen, carbon dioxide, an inert gas, a noble gas, a reactive gas, or any other suitable gas.

Once the plurality of microcapsules are infused and filled with the gas, the microcapsules are exposed to a hydrophobic volatile silane at 314. The silane can include, for example a fluorinated chlorosilane, or any other suitable silane which is evaporated such that the silane deposits into the pores of the microcapsules and seals the pores. Suitable examples of silanes which can be used include but are not limited to n-Octadecyldimethylchlorosilane, tridecafluorooctyl triethoxysilane, hexamethyl-disilazane or any other suitable silane. In other words, the silane acts as a chemical sealant effectively sealing a shell of the microcapsules to trap the gas therewithin. Thus, the silane materials added react with the existing microcapsules to form a shell, i.e. no opening in the capsule. The hydrophobic shell prevents solvent flow into the microcapsule, thus leaving the material within the now shell as an isolated environment. In some embodiments, the gas filled microcapsules are suspended in an aqueous solution which includes a surfactant at 316. For example, the microcapsules can be suspended in water which includes the surfactant such as, for example, PLURONICS®.

Experimental Examples

Preparation of the Oil Droplets (Pre-Inflation)

First, 60 μL $NH_3$ is added to 80 mL deionized water, and 300 μL trimethoxysilyl propyl methacrylate (TPM) oil is added to this solution under mild stirring. After one hour an emulsion consisting of monodisperse 700 nm TPM oil droplets form in the water (hereinafter "the seed emulsion"). The final size of the droplets can be finely adjusted via seeded growth. The seeded growth consist of feeding the seed emulsion with a growing solution prepared as follows: 2.5 ml TPM is added to 50 ml deionized water under mild stirring. After approximately two hours, the solution turns clear, denoting the hydrolysis, and subsequent solubilization of TPM oil.

Seeded Growth (to Tune the Droplets Size)

The growing solution is added to the seed emulsion at a rate of one drop per second. The final size of the oil droplets is typically 1.8 μm. The emulsion is used immediately for the next step. As a grown emulsion ages, it becomes less susceptible to inflation which is attributed to additional siloxane cross-linking.

Inflating the Capsules

The grown emulsion is rapidly added in a ratio of 1:4 (v:v) to a solution of 100 mM NaOH which contains 1 g/L Azobisisobutyronitrile (AIBN). The suspension is capped and shaken vigorously to distribute AIBN as much as possible.

Polymerizing the Capsules

The inflated capsules are put immediately into an oven at 100 degrees Celsius. The polymerization process is over within two hours.

As used herein, the singular forms "a", "an" and "the" include plural referents unless the context clearly dictates otherwise.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method, comprising:
providing an aqueous solution having an alkaline pH;
providing an oil including at least one silsesquioxane compound;
adding the oil to the aqueous solution, the oil forming a plurality of silsesquioxane oil droplets suspended in the aqueous solution, the adding generating an internal osmotic pressure inside the oil droplets by means of a chemical reaction;
allowing the aqueous solution to osmotically diffuse into the plurality of silsesquioxane oil droplets for a predetermined time; and
polymerizing the silsesquioxane oil droplets by cross-linking the at least one silsesquioxane compound included in the silsesquioxane oil droplets to form a plurality of hollow microcapsules containing the aqueous solution therewithin;
removing the plurality of hollow microcapsules from the aqueous solution;
heating the plurality of hollow microcapsules to a temperature in a range of 50 degrees Celsius to 100 degrees Celsius to promote polymerization;
calcinating the plurality of hollow microcapsules at a temperature in a range of 200 degrees Celsius to 700 degrees Celsius; and
refilling the plurality of hollow microcapsules with the aqueous solution.

2. The method of claim 1, wherein the silsesquioxane compound includes at least one of a hydrolysable silane monomer and a low molecular weight silsesquioxane oligomer.

3. The method of claim 2, wherein the at least one silsesquioxane compound includes a compound of formula I:

$$RSiO_{3/2} \qquad (I)$$

where:
Si is silicon;
O is oxygen; and
R is hydrogen, alkyl, alkene, aryl or arylene.

4. The method of claim 1, wherein allowing the aqueous solution to osmotically diffuse into the oil droplets inflates the oil droplets.

5. The method of claim 1, wherein the chemical reaction includes a base catalyzed hydrolysis.

6. The method of claim 1, further comprising:
dissolving a compound in the aqueous solution,
wherein the diffusing urges the compound to also diffuse into the oil droplets such that the plurality of hollow microcapsules contain the compound therewithin with the aqueous solution.

7. The method of claim 6, wherein the compound includes at least one of a fluorescent dye, a pharmaceutical, a nutraceutical, and a polymerizable moiety.

8. The method of claim 1, wherein the plurality of hollow microcapsules have a diameter in the range of 100 nm to 10 microns.

9. The method of claim 1, further comprising:
dissolving a compound into the oil,
wherein a combination of the diffusing and polymerization separates the compound from the oil such that the plurality of hollow microcapsules contain the compound with the aqueous solution contained therewithin.

10. The method of claim 1, further comprising:
suspending nanoparticles in the oil,
wherein the polymerization traps the nanoparticles into a shell of the plurality of hollow microcapsules.

11. The method of claim 1, further comprising:
before refilling the plurality of hollow microcapsules with the aqueous solution, freezing the plurality of hollow microcapsules by:
adding a surfactant to a solution containing the plurality of hollow microcapsules, and adding an acid to the solution to reduce a pH of the
plurality of hollow microcapsules to an acidic pH;
and
adding a base to the solution after a time period to
unfreeze the plurality of hollow microcapsules.

* * * * *